(12) United States Patent
Lee et al.

(10) Patent No.: US 6,586,732 B2
(45) Date of Patent: Jul. 1, 2003

(54) ATMOSPHERIC PRESSURE IONIZATION ION MOBILITY SPECTROMETRY

(75) Inventors: Milton L. Lee, Pleasant Grove, UT (US); David C. Collins, Provo, UT (US)

(73) Assignee: Brigham Young University, Provo, UT (US)

( * ) Notice: Subject to any disclaimer, the term of this patent is extended or adjusted under 35 U.S.C. 154(b) by 228 days.

(21) Appl. No.: 09/788,837

(22) Filed: Feb. 20, 2001

(65) Prior Publication Data

US 2002/0113207 A1 Aug. 22, 2002

(51) Int. Cl.[7] .......................... H01J 49/00; H01J 49/40; B01D 59/44
(52) U.S. Cl. ........................ 250/288; 250/287; 250/286; 250/283; 250/282
(58) Field of Search ................................ 250/288, 287, 250/286, 282, 283

(56) References Cited

U.S. PATENT DOCUMENTS

| | | | |
|---|---|---|---|
| 4,390,784 A | | 6/1983 | Browning et al. |
| 5,581,081 A | * | 12/1996 | Kato et al. .................. 250/288 |
| 5,859,432 A | * | 1/1999 | Kato et al. .................. 250/288 |
| 5,905,258 A | | 5/1999 | Clemmer et al. |
| 5,998,788 A | * | 12/1999 | Breit .......................... 250/286 |
| 6,124,592 A | * | 9/2000 | Spangler ..................... 250/287 |
| 6,236,042 B1 | * | 5/2001 | Kato et al. .................. 250/288 |
| 6,323,482 B1 | * | 11/2001 | Clemmer et al. ........... 250/287 |
| 6,339,218 B1 | * | 1/2002 | Kato et al. .................. 250/288 |
| 6,479,815 B1 | * | 11/2002 | Goebel et al. ............... 250/287 |
| 2002/0014586 A1 | * | 2/2002 | Clemmer ..................... 250/287 |
| 2002/0070339 A1 | * | 6/2002 | Clemmer ..................... 250/299 |

OTHER PUBLICATIONS

Guevremont et al., "Combined Ion Mobility/Time of Flight Mass Spectrometry Study of Electrospray–Generated Ions", Anal. Chem. vol. 69, No. 19, Oct. 1, 1997.
Srebalus et al., "Gas Phase Separations of Electrosprayed Peptide Libraries", Anal. Chem. vol. 71, No. 18, Sep. 15, 1999.
Iinuma et al., "Design of a Continuous Guard Ring and its Application to Swarm Experiments", Rev. Sci. Instrum. 53(6), Jun., 1982.
Carrico et al., "Simple Electrode Design for Ion Mobility Spectrometer", J. Phys. Sci. Instrum., vol. 16, 1983.

* cited by examiner

Primary Examiner—John R. Lee
Assistant Examiner—Bernard E. Souw
(74) Attorney, Agent, or Firm—Greer, Burns & Crain, Ltd.; Philip M. Kolehmainen

(57) ABSTRACT

A high voltage ion propulsion field is applied across the length of an ion mobility spectrometer that is divided by a barrier wall into a desolvation region and a drift tube. A plume of ions and solvent is electrosprayed into the desolvation region, and ions are propelled from the desolvation region through the drift tube to an ion target. Drift gas flows through the drift tube in the opposite direction to oppose the ion flow. A portal in the barrier wall permits ions to move from the desolvation region into the drift tube, and restricts flow of drift gas from the drift tube into the desolvation region. The resulting drift gas velocity increase effects desolvation without requiring elevated temperature or decreased pressure. An ion gate is located near the portal and an aperture grid is located near the ion target. The drift gas flow rate is varied to change the ionization spectra to alter selectivity.

30 Claims, 2 Drawing Sheets

ATMOSPHERIC PRESSURE IONIZATION ION MOBILITY SPECTROMETRY

FIELD OF THE INVENTION

The present invention relates to atmospheric pressure ionization ion mobility spectrometry, for example electrospray ionization ion mobility spectrometry, and more particularly to an improved spectrometer and method for throughput sample screening under ambient conditions.

DESCRIPTION OF THE PRIOR ART

Among the current trends in separation science is reduction of analysis time. Traditional separation methods lose separation quality, in terms of efficiency and resolution, as analysis times are shortened. Conditions adopted for achieving fast separations in liquid chromatography or capillary electrophoresis, such as high pressures and/or electric potentials, can be costly, potentially dangerous and/or can decrease the lifetime of the instrumentation. In addition, compounds which can be separated in minutes can be difficult or impossible to separate more quickly by altering conditions such as mobile phase linear velocity rate or analytical column length. Yet, despite the potential problems, performing fast separations can be very attractive in certain applications. Decreased resolution and separation efficiency may not be detrimental to the analysis, depending on what information is required. If the primary goal is to identify the presence or absence of certain compounds in a simple mixture, a quick screening method may be all that is needed, and a fast separation would be preferred. However, if a complete qualitative and quantitative analysis of all compounds within a mixture is needed, a fast separation may lack the ability to supply all of the necessary information. However, the requirement for thorough analysis may not be known until after a quick screening is performed.

Ion mobility spectrometry (IMS) is a form of gas-phase electrophoresis in which ions are separated based on their mobilities through a drift tube under constant electric potential. Ion mobility is dependent on factors including ion size, charge, and shape. Typically, ions are created at atmospheric pressure and gated through a drift tube against a counter flow of inert drift gas such as air, helium, or nitrogen. Separations occur within milliseconds. Gates are placed at the entrance (and sometimes the exit) of the drift tube and are systematically opened and closed to permit ions to pass through the instrument in such a fashion as to allow desired data to be collected.

Although initially introduced as plasma chromatography, ion mobility spectrometry has been used primarily as a stand-alone detector and has not traditionally been considered to be a useful technique for separating ions due to its relatively low resolution and separation efficiency. IMS performance was not generally considered in terms of chromatographic figures of merit. This may have been, in part, due to the fact that analyses were performed at speeds more representative of detectors rather than conventional separators. In addition, primitive IMS had very poor separation efficiency. Recently, reported efficiencies have improved considerably. These high efficiencies were achieved due to improvements to IMS design, increased electric field homogeneity and detection speed, decreased sample size and gate pulse width and, in some cases, by applying the technique to the analysis of large biomolecules in which electrospray ionization produces multiply charged ions. Recently reported high efficiencies make modern IMS an attractive alternative to other fast separation techniques.

Traditionally, IMS has used radioactive material as an ionizing source. Unfortunately, solely gas-phase compounds could be ionized. U.S. Pat. No. 4,390,784 to Browning et al. discloses an ion mobility detector cell having a reactant region within which gaseous ions are ionized from a gaseous sample and from which ions are injected into a drift tube. An accelerating field is provided by a ceramic tube with a resistive film coating across which a voltage is applied.

Atmospheric pressure ionization (API), including atmospheric pressure chemical ionization (APCI) and electrospray ionization can serve as a source of ions. Only recently has electrospray ionization been adapted to IMS. This has allowed the analysis of liquid samples that contain compounds ranging from low molecular weight to large biomolecules. The principal obstacles to be overcome were, first, the analyte had to be desolvated prior to entrance into the IMS drift tube and, second, a means for keeping the large amounts of solvent being electrosprayed, particularly water, from entering the IMS had to be devised. It has been proposed that these problems be surmounted by the use of a heated or a reduced depressurized desolvation region. APCI also involves the use of solvents and presents similar problems.

U.S. Pat. No. 5,905,258 to Clemmer et al. discloses an ion mobility spectrometer having a drift tube contained in a temperature controlled chamber containing pressurized static buffer gas. Ions are admitted to the drift tube from an ion source wherein a laser is used to desorb gaseous ions from the surface of a sample.

Guevremont et al., "Combined Ion Mobility/Time of Flight Mass Spectometry Study of Electrospray-Generated Ions", Anal. Chem. Vol. 69, No. 19, Oct. 1, 1997, describes an ion mobility spectrometer with an electrospray ion source supplying ions from a chamber through a transfer line to a drift region. A gas stream entering the transfer line is divided, with part entering the drift region, in an attempt to reduce the amount of solvent entering the drift region.

Srebalus et al., "Gas-Phase Separations of Electrosprayed Peptide Libraries", Anal. Chem. Vol. 71, No. 18, Sep. 15, 1999, describes an ion mobility spectrometer in which ions are electrosprayed at atmospheric pressures into a differentially pumped reduced pressure desolvation region and are moved by an electric field through an opposing stream of pumped buffer gas from the desolvation region into a drift tube. The desolvation region includes a series of conductive lenses interconnected by resistors and separated by insulating spacers.

There is a need for an API IMS operable under ambient conditions, for a number of reasons. First, ion mobility spectrometers have been used quite successfully as field-portable instruments due to their robustness, small size, minimal power consumption, and simple means of operation. But with the addition of large heaters or roughing pumps to desolvate electrosprayed ions and to keep the drift tube free of solvent, a degree of portability is lost. Second, in comparison, an IMS that can be operated under ambient conditions is initially less costly and thereafter easier to maintain. Third, heat labile compounds can be analyzed, while a rigorously heated desolvation region limits the analysis of such compounds.

SUMMARY OF THE INVENTION

A principal object of the present invention is to provide an improved ion mobility spectrometry instrument operable for high throughput screening under ambient conditions. Other objects are to provide an API ion mobility spectrometer able to achieve reliable and effective desolvation without special heat or pressure capabilities or complex drift gas ducting; to provide improved API ion mobility spectrometry methods; to provide an API ion mobility spectrometer that is simple and inexpensive relative to known devices without sacrificing performance; and to provide ion mobility spectrometry apparatus and methods overcoming shortcomings of known devices and methods.

In brief, in accordance with the invention there is provided an ion mobility spectrometer including a source of ions and solvent and a desolvation region receiving ions and solvent from the source. A drift tube has an ion inlet end and an ion outlet end. An ion transfer portal is located between the desolvation region and the drift tube inlet end. An ion propulsion field is applied along the drift tube. A drift gas inlet is adjacent the drift tube outlet end and a drift gas outlet is in the desolvation region. The ion transfer portal includes a wall separating the desolvation region from the drift tube, and an aperture in the wall providing a restricted drift gas flow path from the drift tube to the desolvation region.

BRIEF DESCRIPTION OF THE DRAWING

The present invention together with the above and other objects and advantages may best be understood from the following detailed description of the preferred embodiment of the invention illustrated in the drawings, wherein:

FIG. 3 is an enlarged sectional view of one conductive ring of the ion mobility spectrometer;

FIG. 4 is a side elevational view of the ion gate and drift gas portal of the ion mobility spectrometer viewed from the line 4—4 of FIG. 2; and FIG. 5 is a side elevational view of the aperture grid and ion outlet end of the ion mobility spectrometer viewed from the line 5—5 of FIG. 2.

DETAILED DESCRIPTION OF THE PREFERRED EMBODIMENTS

Figure 1:
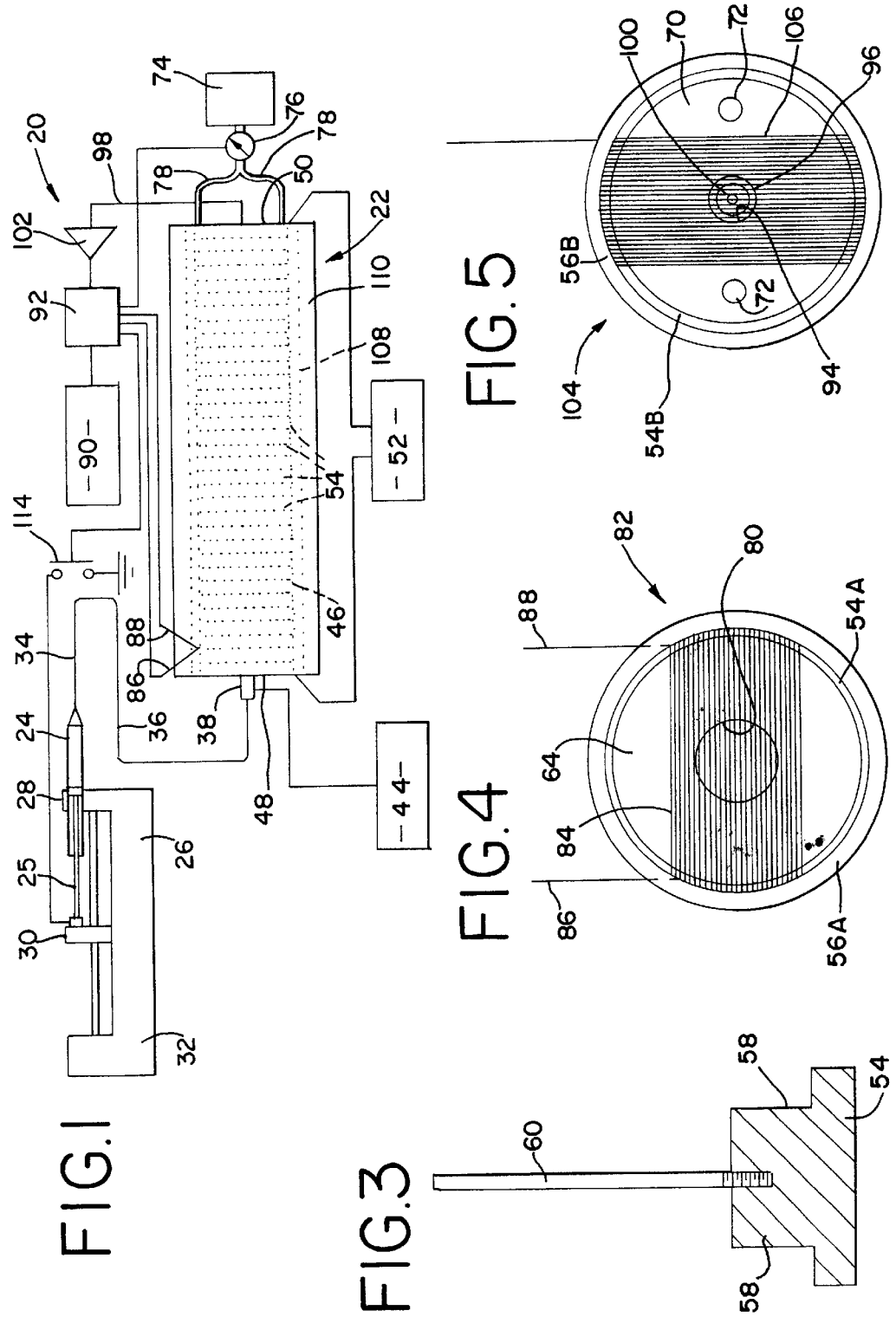
FIG. 1 is a schematic block diagram of a sample screening system including an ion mobility spectrometer constructed in accordance with the present invention.

Having reference now to the drawings and initially to FIG. 1 there is illustrated a sample screening system designated as a whole as 20 and including an electrospray ionization ion mobility spectrometer generally designated as 22 constructed in accordance with the principles of the present invention. A source of ions and solvent such as an atmospheric pressure chemical ionization source could be used in place of the illustrated electrospray ionization source described below. The ion mobility spectrometer (IMS) 22 operates at high throughput screening rates and in ambient conditions.

In the illustrated IMS 22, an electrospray solution including a sample to be screened and a solvent is introduced into the system 20 by a syringe 24 having a metal plunger 25. A syringe pump 26 includes a syringe holder 28, a plunger drive plate 30 and a motor assembly 32. The motor assembly 32 is operated to move the drive plate 30 and force the electrospray solution from the syringe 24 through a needle 34 and through a conduit 36 to an ion injection spray tip 38. In a preferred embodiment of the invention, the syringe 24 is a 250 $\mu$L GASTIGHT syringe with a 22 gauge needle 34 available from Hamilton Company, P. O. Box 10030, Reno, Nev. The syringe pump 26 is a Model 55-2222 pump available from Harvard Apparatus, Inc., 84 October Hill Road, Holliston, Mass. 01746.

The ion injection spray tip 38 includes a fused silica capillary 40 (FIG. 2) held by a conductive metal union 42. In the preferred arrangement, the capillary 40 has in inside diameter of 20 $\mu$m and an outside diameter of 80 $\mu$m. A dc power supply 44 applies a high voltage, preferably about 20 kV, to the union 42. The electrospray solution flows through the spray tip 38 at a flow rate in the approximate range of 0.3 to 0.5 $\mu$L per minute. The solution liquid is atomized by expulsion form the capillary 40 and polar compounds in the solution are ionized by the voltage applied by power supply 44.

A plume of charged ions and solvent is introduced into the IMS 22 from the ion injection spray tip 38. In general, the IMS 22 includes an axially elongated tubular body 46 having a first, ion input end 48 and a second, ion output end 50. An electrical field is established in an axial direction along the body 46 to accelerate and propel ions away from the ion input end 48 and toward the ion output end 50. A high voltage, preferably about 17 kV, is applied across opposite ends 48 and 50 of body 46 by a dc power supply 52. In the preferred arrangement, the power supplies 44 and 52 are Bertan 20 kV Series 230 power supplies available from Bertan High Voltage Corp., 121 New South Road, Hicksville, N.Y. 11801.

Figure 2:
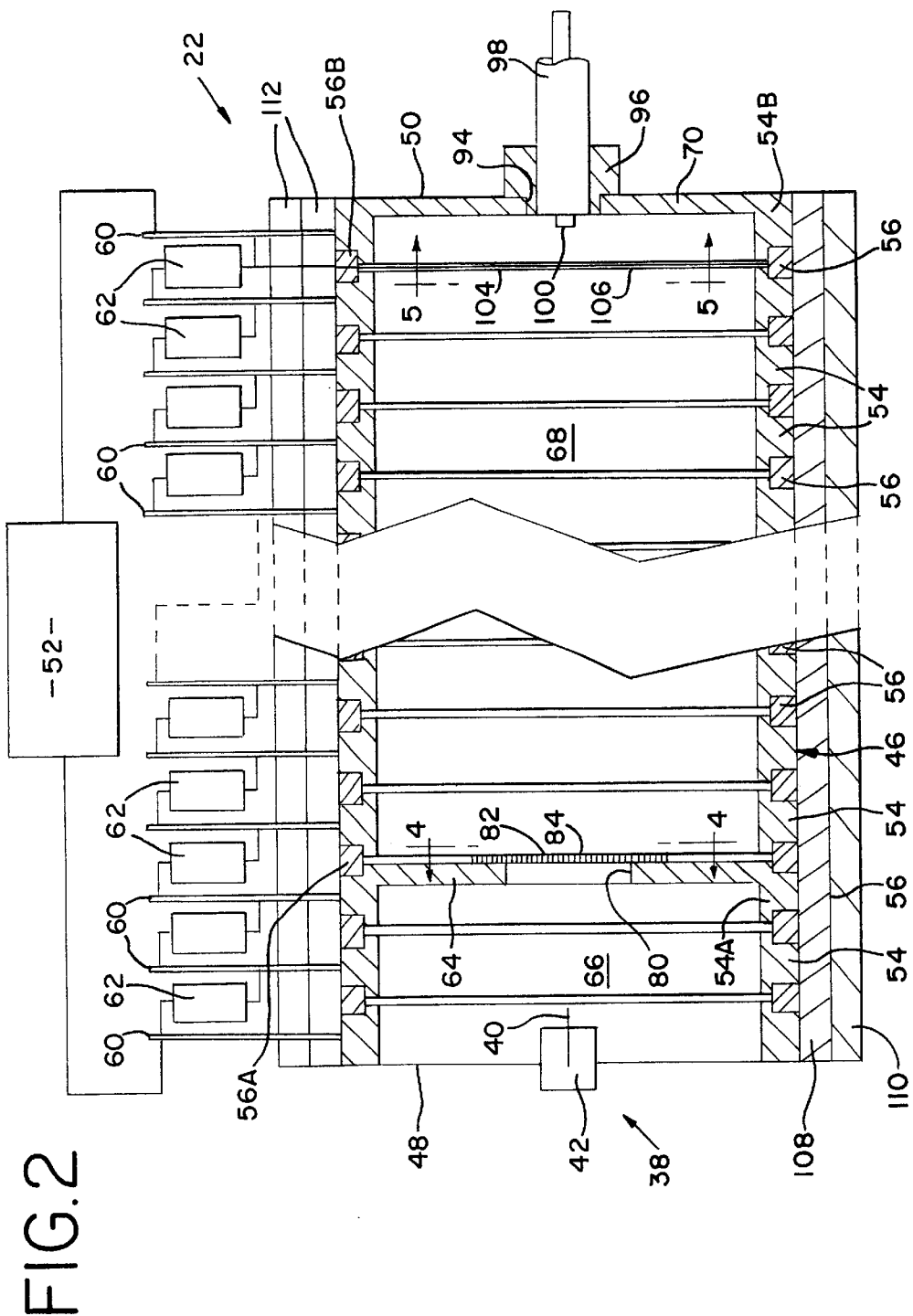
FIG. 2 is an enlarged, fragmentary, axial cross sectional view of the ion mobility spectrometer of FIG. 1, with the central portion omitted.

The IMS body 46 includes electrically conductive and electrically resistive material distributed uniformly throughout its length in order to distribute the applied electrical potential in an ion propulsion field along the axial direction along the length of the body 46. As seen in FIG. 2, the body 46 is a right circular cylinder made up of several conductive stainless steel rings 54 separated by insulating ceramic spacers 56. In the preferred arrangement, the rings 54 have an inside diameter of 4.8 cm, an outside diameter of 5.7 cm and an axial length of 0.8 cm. Grooves 58 (FIG. 3) are formed in the outer shoulders of the rings 54 in order to receive the spacers 56. In the preferred embodiment the spacers have an inside diameter of 5.7 cm and an axial length sufficient to establish a spacing of 0.08 cm between adjacent rings. The IMS body 46 is small and easily moved, including 34 rings 54 and 33 spacers 56 for an axial length of about 30 cm.

As best seen in FIG. 3, each stainless steel ring 54 is provided with a radially extending electrical terminal post 60. Preferably the terminal posts 60 are threaded into mating openings provided in the outer periphery of each ring 54. As seen in FIG. 2, a resistor 62, preferably a high voltage 10M$\Omega$ resistor, is connected between the terminal posts 60 of each adjacent pair of rings ring 54. The rings 54, separated by resistors 62, are connected in series across the power supply 52.

Another way to provide distributed conductivity and resistivity along the length of the body 46 is to use a ceramic or similar body with its interior coated with a thick film resistor. Constructions of this type are disclosed in Iinuma et al., "Design of a Continuous Guard Ring and its Application to Swarm Experiments", Rev. Sci. Instrum. 53(6), June, 1982, and in Carrico et al., "Simple Electrode Design for Ion Mobility Spectrometer", J. Phys. Sci. Instrum., Vol. 16, 1983 and in U.S. Pat. No. 4,390,784, all three of which are incorporated herein by reference.

A barrier wall 64 divides the interior of the tubular body 46 into a desolvation chamber or region 66 adjacent the ion inlet end 48 and a drift tube 68 adjacent the ion outlet end 50. The barrier wall 64 is provided as the inner part of a stainless steel ring 54A that is spaced inward from the ion inlet end 48 of the body 46. Preferably the ring 54A is the third ring 54 from the ion inlet end 48, and the desolvation chamber, to the left of the wall 64 in FIG. 2, has an axial length of about 2.5 cm. The drift tube 68, to the right of the wall 64 in FIG. 2, has an axial length of about 27 cm.

The ion outlet end 50 of the body 46 is closed by an end wall 70 provided as part of a stainless steel ring 54B at the end 50. The end wall 70 includes a pair of drift gas inlet ports 72 seen in FIG. 5. The sample screening system 20 (FIG. 1) includes a source 74 of pressurized inert gas such as air, helium or nitrogen, preferably nitrogen. The drift gas source 74 communicates with the drift gas inlet ports 72 through a variable flow control valve 76 and drift gas supply conduits 78.

The axially directed distributed electrical field applied to body 46 by the power supply 52 propels the ions injected by the spray tip 38 toward the ion exit end 50 of the body. The variable flow valve 76 is operated to supply drift gas under pressure to the drift gas inlet ports 72, and the drift gas flows through the body 46 toward the ion inlet end 48, opposing the ion flow.

In accordance with the present invention, the barrier wall 64 between the desolvation chamber 66 and the drift tube 68 is provided with an opening or portal 80. Portal 80 is centrally located in the wall 64, coaxial with the desolvation chamber 66 and the drift tube 68. While the desolvation chamber 66 and the drift tube 68 have similar, relatively large inside diameters, the portal 80 has a relatively smaller diameter. The portal 80 permits the movement of ions from the desolvation chamber 66 through the barrier 64 and into the drift tube 68. The portal 80 also permits the flow of drift gas in the opposite direction from the drift tube 68 through the barrier 64 and into the desolvation chamber 66. Due to its reduced size and cross sectional area relative to the drift tube 68 and the desolvation chamber 66, the portal 80 is a flow restriction in the path of flow of drift gas. The flow restriction provided by the barrier wall 64 and the portal 80 has important advantages in the operation of the IMS 22.

Solvent contamination of the drift tube 68 interferes with separation efficiency and resolution during operation of the IMS 22. Therefore it is desirable to prevent the movement of solvent from the injection spray tip plume into the drift tube 68. The goal is to remove as much solvent as possible in the desolvation chamber 66. The reduced diameter portal 80 improves desolvation performance in two ways. First, because of the reduced size of the flow path from the desolvation chamber 66 to the drift tube 68 (to the right as viewed if FIG. 2), the barrier wall 64 partially blocks the movement of solvent through the portal 80 and decreases the size of the path through which solvent could enter the drift tube 68. Second, the portal 80 provides a flow restriction in the flow path of drift gas from the drift tube 68 to the desolvation chamber 66 (to the left as viewed in FIG. 2). This flow restriction produces an increase in the velocity of drift gas flowing through the portal 80. This increased velocity drift gas flow strips solvent from the ion stream traveling in the opposite direction and opposes flow of solvent while not appreciably decreasing ion flow.

By using the barrier wall 64 with the restricted flow portal 80, it is possible to achieve a high level of desolvation of the electrospray plume. As a result the IMS 22 can operate under ambient conditions. The expense, size, inconvenience and possibly hazardous nature of other desolvation approaches such as high temperatures or low pressures are avoided.

Another advantage of the barrier wall 64 and portal 80 is that they can be employed to overcome the problem of contamination of the drift tube 68 during periods of non use. While the IMS 22 is inactive, the flow control valve 76 is adjusted to provide a low volume flow through the portal 80 from the drift tube 68 to the desolvation chamber 66. This flow, although using only a small quantity of drift gas, has sufficient velocity at the portal 80 to minimize the diffusion of laboratory air into the drift tube. The accuracy of the instrument is maintained and the need for drift tube cleaning and maintenance is reduced. A low standby flow rate of only about 100 mL per minute is sufficient for this purpose.

The size of the portal 80 can be optimized for best performance. It has been found that if the diameter of the portal 80 is not appreciably smaller than the diameter of the body 46, the desired desolvation performance is not obtained. The diameter of the portal should be less than about one-half, and preferably about one-third, of the body diameter. With a drift tube diameter and desolvation chamber diameter of 4.8 cm, a portal diameter of 1.6 cm achieved good resolution and signal intensity in the operation of the IMS 22. If the portal diameter is decreased much beyond the preferred one-third diameter, then signal intensity decreases with no apparent increase in resolution. Use of the restricted aperture portal 80 reduces peak tailing and increases peak resolution, without appreciable loss of signal intensity.

An ion gate 82 (FIGS. 2 and 4) alternatively blocks and permits the movement of ions into the drift tube 68. An insulating spacer 56A adjacent to the ring 54A having the barrier wall 64 supports the ion gate 82. The gate is a closely spaced array of fine wire 84 forming a grid covering the portal 80 as seen in FIG. 4. Preferably the gate 82 includes two separate lengths of 0.1 mm diameter stainless steel wire with chordal segments parallel to one another and spaced on 0.6 mm centers. Alternate wire segments are electrically interconnected, providing a pair of interspersed conductive wire patterns. Wire terminal portions 86 and 88 extend outwardly from the body 46.

The ion gate 82 and other components of the screening system 20 are controlled by a controller 90 (FIG. 1) preferably including a computer having a programmable microprocessor and memory, display and user input capabilities. The controller 90 is interfaced with components of the screening system 20 through an analog and digital input/output device 92, such as a Model PCI 6023E data acquisition board available from National Instruments Corporation, 11500 N. Mopac Expressway, Austin, Tex. 78759.

To open the ion gate 82 and permit entry of ions into the drift tube 68, the controller 90 and device 92 apply to the wire terminals 86 and 88 a gate bias voltage equal to the voltage within the IMS electrical field at the location of the gate 82. In the preferred arrangement, the voltage at the entry of the drift tube 68 is about 15 kV, and this same voltage is applied to the gate 82 in the open state. To close the gate 82 and prevent the flow of ions into the drift tube 68, the controller 90 and interface device 92 apply higher and lower voltages to the wire ends 86 and 88. The voltage increase/decrease, of preferably about plus and minus 40 volts, results in an electrical field greater than and orthogonal to the ion propulsion field of the drift tube. Ions entering through the portal 80 are captured by the grid of the ion gate 82 and cannot continue along the path through the drift tube 68. Typically the ion injection spray tip 38 is operated continuously while the ion gate 82 is operated at a frequency of 20 Hz, with a gate opening pulse width of 0.2 ms. A burst of ions is admitted to the drift tube during each gate open pulse.

The end wall 70 at the ion exit end of the body 46 includes a central ion target opening 94. In the illustrated screening system 20, the opening 94 receives a sleeve 96 supporting the end of a cable 98, preferably a low noise BNC coaxial cable. The central conductor of the cable 98 is connected to an electrically grounded Faraday plate ion target 100 that is exposed at the center of the wall 70. Ions propelled by the ion propulsion field of the IMS 22 strike the target plate 100 as an electrical current. The intensity of the current varies with ion density in a pattern determined by ion mobility characteristics including size, charge and shape. The resulting spectrum is used to identify compounds present in the electrospray solution. For this purpose, the detected current is amplified by an amplifier 102 (FIG. 1) and supplied for display, recording and the like to the controller 90 through an input of the input/output device 92. The amplifier 102 may be a Model 428 current amplifier available from Keithley Instruments, Inc., 28775 Aurora Road, Cleveland, Ohio 44139.

An aperture grid 104 in front of the ion target 100 reduces peak fronting by eliminating premature induced current within the target plate 100 occurring prior to ions striking the plate 100. An insulating spacer 56B adjacent to the ring 54B with the end wall 70 supports the aperture grid 104. The grid 104 is a closely spaced screen of fine wire 106 covering most of the cross section of the drift tube 68 in front of the ion target plate 100 (FIG. 5). Preferably the grid 104 includes a single continuous length of 0.1 mm diameter stainless steel wire with adjacent chordal segments parallel to one another and spaced on 0.6 mm centers. A wire terminal portion 108 is connected to the ring 54B (FIG. 2) and is at the same electrical potential. Current induced in the region of the target plate 100 by moving ions is induced in the aperture grid 104 and not in the target plate 100.

The body 46 is enclosed in a surrounding sleeve 108 of ceramic material, and the sleeve 108 is in turn surrounded by a cylindrical body 110 of aluminum. The sleeve 108 and body 110 have an axially extending open slot 112 providing clearance for the terminal posts 60. The body 110 can be heated to serve as an oven for occasional baking of the drift tube 68 to drive off any compounds or solvent that may have absorbed onto the drift tube 68 during operation or cleaning.

The IMS 22 can by used in applications other than for screening samples with the ion target plate 100. The target opening 94 can be unobstructed and/or provided with an ion optics system and used to transmit separated ion groups to other instruments such as a time-of-flight mass spectrometer or other mass spectrometer. The advantages of the IMS 22 achieved with the present invention are applicable to many applications.

In order to increase the ability to resolve peaks of interest for given samples, the rate of flow of drift gas through the drift tube 68 is varied. The variable flow control valve 76 can be operated by the controller 90, or manually if desired, to vary the flow rate of drift gas in the drift tube 68. The flow rate can be varied, for example, in the range of about 100 to about 1800 mL per minute. Depending on the identity of the ion or ions of interest, it is possible to selectively increase resolution and separate overlapping peaks by changing the drift gas flow rate. For example, in analysis of spectra of benzodiazepines in nitrogen drift gas, it was found that peaks of oxazepam and diazepam that were overlapping and indistinguishable at low flow rates of about 100 or even 500 mL per minute were separated and readily distinguishable at higher flow rates of over 1,000 mL per minute. This approach offers one way to alter the selectivity of ions within the drift tube 68.

A high voltage is used for ionization with the ion injection spray tip 38. The normal flow of current in the IMS 22 is the travel of charged ions from the tip 38 through the desolvation chamber 66, the portal 80 and the drift tube 68 to the electrically grounded ion target plate 100. The character of the spectra obtained using the IMS 22 can be changed by adding a second, parallel current path. This is done by establishing a path to ground from the syringe 24. A switch 114 can be closed, either by the controller 90 or manually, in order to connect the metal syringe plunger 25 to ground. A small current can then flow from the tip 38 through the electrospray solution in the conduit 38 to the syringe and then to ground through the syringe plunger 25 and switch 114 to ground. When the second current path is enabled, the spectra changes can include ionization suppression of some compounds. This can be an advantage in removing overlaid peaks and detecting other peaks that are not suppressed.

While the present invention has been described with reference to the details of the embodiment of the invention shown in the drawing, these details are not intended to limit the scope of the invention as claimed in the appended claims.

What is claimed is:

1. An ion mobility spectrometer comprising:
    a source of ions and solvent;
    a desolvation region receiving ions and solvent from said source;
    a drift tube having an ion inlet end and an ion outlet end;
    an ion transfer portal between said desolvation region and said drift tube inlet end;
    means for applying an ion propulsion electrical field along said drift tube;
    a drift gas inlet adjacent said drift tube outlet end and a drift gas outlet in said desolvation region; and
    said ion transfer portal including a wall separating said desolvation region from said drift tube, and an aperture in said wall providing a restricted drift gas flow path from said drift tube to said desolvation region.

2. An ion mobility spectrometer as claimed in claim 1 further comprising an ion gate overlying said ion transfer portal.

3. An ion mobility spectrometer as claimed in claim 2, said ion gate being located at said drift tube inlet end.

4. An ion mobility spectrometer as claimed in claim 1, said source of ions and solvent comprising an electrospray tip.

5. An ion mobility spectrometer as claimed in claim 1 further comprising an aperture grid in said drift tube adjacent said ion outlet end.

6. An ion mobility spectrometer as claimed in claim 1 further comprising a variable flow drift gas supply connected to said drift gas inlet.

7. An ion mobility spectrometer as claimed in claim 1 further comprising an ion target located at said ion outlet end of said drift tube.

8. An ion mobility spectrometer as claimed in claim 7, said ion target comprising a Faraday plate.

9. An API ion mobility spectrometer comprising:
    an elongated generally tubular body having an ion source end and an ion target end and a longitudinal axis extending between said ends;
    said body including a desolvation chamber adjacent said ion inlet end and a drift chamber adjacent said ion target end;
    an API ion source disposed at said ion source end for introducing ions and solvent into said desolvation chamber;

a voltage source connected to apply a voltage differential to said ends of said body;

said body including electrically conductive and resistive materials distributed along its length applying said voltage differential as an ion propulsion field acting in a first direction within said body along said longitudinal axis to propel ions from said ion source end to said ion target end;

a drift gas inlet disposed at said ion target end for admitting drift gas to flow through said drift chamber and said desolvation chamber in opposition to the flow of ions;

a barrier wall in said body extending transverse to said longitudinal axis and separating said drift chamber from said desolvation chamber; and an aperture in said barrier wall permitting flow of ions from said desolvation region into said drift chamber while restricting the flow of drift gas from said drift chamber to said desolvation region.

10. The API ion mobility spectrometer of claim 9, said body having a uniform cross section throughout its length.

11. The API ion mobility spectrometer of claim 9, said aperture having a diameter smaller than about one-half the diameter of said drift tube.

12. The API ion mobility spectrometer of claim 11, said aperture having a diameter not larger than about one-third of the diameter of said drift tube.

13. The API ion mobility spectrometer of claim 12, said aperture having a diameter of about one-third the diameter of said drift tube.

14. The API ion mobility spectrometer of claim 12, said desolvation region having a cross sectional area equal to the cross sectional area of said drift tube.

15. The API ion mobility spectrometer of claim 9, said body including a side wall including conductive rings separated by insulating spacers, one of said rings supporting said barrier wall.

16. The API ion mobility spectrometer of claim 9, said body including a side wall of insulating material with a lining of resistor film.

17. The API ion mobility spectrometer of claim 15, one of said spacers immediately adjacent to said one ring supporting an ion gate overlying said aperture.

18. The API ion mobility spectrometer of claim 17, said ion gate including an array of wire carried by said one spacer.

19. The API ion mobility spectrometer of claim 18, a second of said spacers adjacent to said ion target end including an aperture grid.

20. The API ion mobility spectrometer of claim 19, said aperture grid including an array of wire carried by said second spacer.

21. The API ion mobility spectrometer of claim 9, further comprising a variable flow drift gas source connected to said drift gas inlet.

22. The API ion mobility spectrometer of claim 9, further comprising an ion target at said ion target end of said body.

23. The API ion mobility spectrometer of claim 22, further comprising an end wall at said ion target end of said body, said ion target comprising an opening in said end wall.

24. The API ion mobility spectrometer of claim 22, further comprising an end wall at said ion target end of said body, said ion target comprising a Faraday plate supported by said end wall.

25. The API ion mobility spectrometer of claim 9, said API in source comprising an electrospray ionization ion source, a syringe for forcing an electrically conductive electrospray solution through said electrospray ion source, and means for grounding said syringe to complete a current flow path from ground to said electrospray ion source.

26. A method for ion mobility spectrometry comprising the steps of:

injecting ions and solvent into a desolvation chamber at a first end of an axially extending ion accelerator body;

applying an electrical field to the ion accelerator body to propel ions from the desolvation chamber and through a drift tube toward a second end of the body;

flowing a drift gas from the second end of the body through the drift tube and desolvation region to the first end of the body;

partially blocking the flow of drift gas from the drift tube to the desolvation chamber with a flow barrier, and providing a restricted flow of drift gas from the drift tube to the desolvation chamber through an aperture in the flow barrier.

27. The method of claim 26 further comprising:

gating the flow of ions from the desolvation chamber to the drift tube.

28. The method of claim 27 further comprising detecting the arrival of ions at the second end of the body.

29. The method of claim 26 further comprising:

varying the flow rate of drift gas in the body in order to alter the selectivity of the ion mobility spectrum.

30. A method for ion mobility spectrometry comprising the steps of:

injecting ions into a first end of an axially extending ion accelerator body;

applying an electrical field to the ion accelerator body to propel ions from the first end and through a drift tube toward a second end of the body;

introducing a flow of drift gas into the body;

flowing the drift gas from the second end of the body through the drift tube and desolvation region to the first end of the body; and varying the rate at which drift gas is introduced into the body in order to alter the selectivity of the ion mobility spectrum.

* * * * *